United States Patent [19]

Siegel et al.

[11] Patent Number: 5,347,047
[45] Date of Patent: Sep. 13, 1994

[54] PREPARATION OF ACYLAROMATIC COMPOUNDS

[75] Inventors: Wolfgang Siegel, Mannheim; Irene Troetsch-Schaller, Frankenthal, both of Fed. Rep. of Germany

[73] Assignee: BASF Aktiengesellschaft, Ludwigshafen, Fed. Rep. of Germany

[21] Appl. No.: 158,776

[22] Filed: Dec. 1, 1993

[30] Foreign Application Priority Data

Dec. 5, 1992 [DE] Fed. Rep. of Germany ....... 4240965

[51] Int. Cl.$^5$ ................ C07C 59/76; C07C 45/00
[52] U.S. Cl. ................ 562/460; 568/319
[58] Field of Search ................ 568/319; 562/460

[56] References Cited

U.S. PATENT DOCUMENTS

| | | | |
|---|---|---|---|
| 2,645,663 | 7/1953 | Newton | 568/319 |
| 2,773,903 | 12/1956 | Hardy et al. | 260/591 |
| 2,879,297 | 3/1959 | Prill et al. | 568/319 |
| 3,651,099 | 3/1972 | Perlinger et al. | 260/377 |
| 3,962,326 | 6/1976 | Semier et al. | 260/377 |
| 4,141,995 | 2/1979 | Saunders | 568/319 |
| 4,670,603 | 6/1987 | Piccolo et al. | 568/319 |
| 4,714,781 | 12/1987 | Gupta | 568/319 |
| 5,041,616 | 8/1991 | Sumner, Jr. | 560/144 |

FOREIGN PATENT DOCUMENTS

| | | |
|---|---|---|
| 512363 | 4/1955 | Canada . |
| 2049908 | 1/1992 | Canada . |
| 069598 | 1/1983 | European Pat. Off. . |
| 075390 | 3/1983 | European Pat. Off. . |
| 178184 | 4/1986 | European Pat. Off. . |
| 2057956 | 6/1972 | Fed. Rep. of Germany . |
| 2321122 | 11/1974 | Fed. Rep. of Germany . |
| 717720 | 11/1954 | United Kingdom . |
| 1066542 | 4/1967 | United Kingdom . |
| 1164046 | 9/1969 | United Kingdom . |
| 1361018 | 7/1974 | United Kingdom . |

OTHER PUBLICATIONS

Synthesis (1972) 531.

*Primary Examiner*—Paul J. Killos
*Attorney, Agent, or Firm*—Keil & Weinkauf

[57] ABSTRACT

Acylaromatic compounds are prepared from aromatic compounds and carboxylic acids by reacting the starting compounds with phosgene in the presence of an aliphatic phosphine oxide or of an N,N-dialkylformamide and of an Fe(II), Fe(III) or Zn(II) compound.

4 Claims, No Drawings

PREPARATION OF ACYLAROMATIC COMPOUNDS

The present invention relates to a novel process for preparing acylaromatic compounds from aromatic compounds and carboxylic acids.

Several condensing agents are known for the acylation of aromatic compounds with carboxylic acids.

At least two equivalents of $AlCl_3$ or 1.5 equivalents of $ZnCl_2$ are required per equivalent of carboxylic acid in such reactions (Houben-Weyl, Methoden der organischen Chemie, Thieme Verlag, Stuttgart 1973, Vol. 7/2a, pages 281 and 284). Not only are these above-stoichiometric amounts uneconomic, they also lead, on conventional workup with water, to heavy loading of the waste water from the process with metal and chloride ions.

Reactive aromatic compounds such as phenols or phenol ethers can also be acylated using a polyphosphoric acid in large excess (Houben-Weyl, loc. cit., pages 20 and 299). An excess of hydrogen fluoride is recommended as condensing agent in GB 11 64 046.

At least equimolar amounts of Lewis acids such as halides of boron, titanium, niobium, tantalum, phosphorus, arsenic and antimony are described as condensing agents in combination with a strong acid in EP-A 69 598.

EP-A 75 390 discloses the preparation of benzoylaromatic compounds using, preferably, a stoichiometric amount of a fluoroalkanesulfonic acid.

Substoichiometric amounts of sulfonic acids are sufficient as condensing agents for preparing aryl ketones if the water formed during the reaction is removed azeotropically from the reaction mixture (U.S. Pat. No. 5,041,616). The reaction mixture in this case is worked up with water, and the solvent required for the azeotropic distillation must be removed.

DE-A 23 21 122 and DE-A 20 57 956 disclose the reaction of carboxylic acids with phosgene to give carbonyl halides in the presence of aliphatic phosphine oxides or N,N-dialkylformamides.

The use of catalytic amounts of Fe and Zn compounds and of iodine for acylation of aromatic compounds with carbonyl chlorides is disclosed by Pearson et al. in Synthesis (1972) 531.

It is an object of the present invention to provide a process for the acylation of aromatic compounds with carboxylic acids without the need for stoichiometric amounts of a Lewis acid in combination with a condensing agent. In addition, the reaction mixture ought to be amenable to non-hydrolytic workup.

We have found that this object is achieved by a process for preparing acylaromatic compounds from aromatic compounds and carboxylic acids, which comprises reacting the starting compounds with phosgene in the presence of an aliphatic phosphine oxide or of an N,N-dialkylformamide and of an Fe(II), Fe(III) or Zn(II) compound.

The reaction is outlined by the following equation:

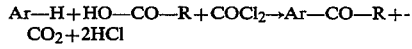

Ar=aromatic radical
R=organic radical

The aromatic compounds suitable for the reaction comprise benzene, naphthalene, anthracene and other polycyclic aromatic hydrocarbons as well as derivatives thereof. The preferred substituents are $C_1$–$C_{20}$-alkyl groups such as methyl, ethyl, isopropyl, tert-butyl and tert-amyl, $C_6$–$C_{10}$-aryl groups such as phenyl, $C_1$–$C_{20}$-alkoxy such as methoxy, ethoxy, isopropoxy, aryloxy such as phenoxy, $C_1$–$C_{20}$-alkylthio such as methylthio, ethylthio and propylthio, hydroxyl and halogen such as fluorine, chlorine and bromine, acyl groups, which can also have been introduced by the process according to the invention, such as 2-haloacyl, e.g. 2-chloroacetyl, 2-chloropropionyl, 2-chlorobutanoyl or aroyl such as benzoyl, 4chlorobenzoyl, 4-fluorobenzoyl, 2-methylbenzoyl, 3methylbenzoyl and 4-methylbenzoyl. The aromatic compounds can have one or more substituents which may differ from one another.

Compounds for which the process according to the invention has particular importance are: benzene, toluene, o-xylene, m-xylene, p-xylene, tertbutylbenzene, diphenyl ether, anisole, 1-tert-amyl-4-methylbenzene, 1,3-dimethoxybenzene, 1-tert-butyl-4-methylbenzene, chlorobenzene, 1,2-dimethoxybenzene, 1,3,5-trimethylbenzene and 1,2,4,5-tetramethylbenzene.

The carboxylic acids used in the process according to the invention are not subject to any evident restrictions. Preferred carboxylic acids are, however, aromatic carboxylic acids, especially benzoic acid or benzoic acids with inert substituents. These inert substituents comprise $C_1$–$C_{20}$-alkyl such as methyl, ethyl, propyl, $C_6$–$C_{10}$-aryl such as phenyl and naphthyl, $C_1$–$C_{20}$-alkoxy such as methoxy, ethoxy, isopropoxy, $C_6$–$C_{10}$-aryloxy such as phenoxy, carboxyl and halogen such as fluorine, chlorine, bromine. These substituents can occupy position 2, 3 and/or 4 of the carboxylic acids. Examples to be mentioned are: benzoic acid, 2-, 3- and 4-methylbenzoic acid, phthalic acid, isophthalic acid, terephthalic acid, 2-, 3- and 4-chlorobenzoic acid, 4-methoxybenzoic acid, 4-fluorobenzoic acid and 4-phenoxybenzoic acid.

Also preferred are α-haloalkanoic acids such as chloroacetic acid, 2-chloropropionic acid, 2-chlorobutyric acid, bromoacetic acid, 2-bromopropionic acid and 2-bromobutyric acid.

The reaction takes place in the presence of an aliphatic phosphine oxide or of an N,N-dialkylformamide.

The aliphatic phosphine oxides are preferably trialkylphosphine oxides with straight-chain or branched radicals with 1–12 carbons. Tri-n-butylphosphine oxide, tri-n-hexylphosphine oxide and tri-n-octylphosphine oxide are particularly preferred.

Preferred N,N-dialkylformamides are those with $C_1$–$C_{30}$-alkyl chains, particularly preferably di-sec-butylformamide.

The metal compounds complying with the definition are also used in the reaction. These are Fe(II) compounds such as $FeSO_4$, Fe(III) compounds such as $FeCl_3$, $FeBr_3$, $Fe_2(SO_4)_3$, iron(III) acetylacetonate, iron(III) carboxylates such as benzoate and acetate, and mixed valency compounds such as $Fe_3O_4$ and, preferably, $Fe_2O_3$. Also suitable are zinc(II) compounds such as $ZnCl_2$, $ZnBr_2$, ZnO and zinc carboxylates such as zinc benzoate and zinc acetate.

The carboxylic acid is generally used in equimolar amount or slightly above or below this relative to the aromatic compound. The preferred molar ratio of carboxylic acid to aromatic compound is from 1:1 to 0.8:1.

The phosphine oxide or the N,N-dialkylformamide is usually employed in amounts of from 0.1 to 5 mol %, preferably from 1 to 2 mol %, based on the amount of aromatic compound. The transition metal compound generally used in amounts of from 0.1 to 10 mol %, preferably from 1 to 3 mol %, based on the amount of aromatic compound.

Phosgene is normally employed in the stoichiometric amount or in a slight molar excess based on the amount of carboxylic acid. From 1.05 to 1.2 mol of phosgene per mol of carboxylic acid is preferred.

It has proven suitable to carry out the reaction by mixing the aromatic compound and carboxylic acid with the aliphatic phosphine oxide or the N,N-dialkylformamaide and the Fe(II), Fe(III) or Zn(II) compound and, at 100°–120° C., to add the phosgene. After a reaction time of about one hour, excess phosgene is removed in a stream of nitrogen, and the reaction is completed by heating further.

The reaction is generally carried out at from 50° to 200° C., preferably from 100° to 180° C. The reaction can be carried out under a pressure of up to about 10 bar, but it is normally carried out at atmospheric pressure. The reaction is generally complete after from 4 to 20 hours. It can be carried out in inert solvents such as nitrobenzene or hydrocarbons such as heptane, octane, nonane, decane or mixtures thereof, but it is preferably carried out without solvent.

The products can be isolated from the reaction mixture by conventional procedures such as crystallization or distillation.

The process according to the invention allows acyl compounds to be prepared from aromatic compounds and carboxylic acids in only one step, and only catalytic amounts of a Lewis acid in combination with phosgene are required. The process can be carried out without solvent. The products can be isolated without working up with water.

The products are important intermediates, e.g. for dyes, and antioxidants.

EXAMPLES

General preparation method 1.2 mol of an $R^1,R^2$-disubstituted benzene, 1 mol of a substituted benzoic acid $R^3$—$C_6H_4$—COOH, 2 mol % of an N,N-dialkylformamide or of a phosphine oxide and 3 mol % of $Fe_2O_3$ were mixed and heated to 100°–120° C. 1.1 mol of phosgene were passed in. After one hour, excess phosgene was removed in a stream of nitrogen, and the solution was heated at T° C. for t hours. The resulting acylaromatic compounds were isolated by distillation or crystallization from heptane.

TABLE

| Example | Benzene $R^1$ | $R^2$ | Benzoic acid $R^3$ | Addition | t [h] | T [°C.] | Product (-benzophenone) | Yield [%] |
|---|---|---|---|---|---|---|---|---|
| 1 | tert-butyl | H | 2-methyl | DsBF | 8 | 130 | 4-butyl-2'-methyl | 80 |
| 2 | tert-butyl | H | 4-methyl | TOPO | 10 | 140 | 4-butyl-4'-methyl | 60 |
| 3 | phenoxy | H | 2-methyl | TOPO | 5 | 130 | 2-methyl-4'-phenoxy | 75 |
| 4 | phenoxy | H | 4-COOH | DsBF | 15 | 180 | 4-carboxyl-4'-phenoxy | 50 |
| 5 | Cl | H | 2-methyl | TOPO | 10 | 130 | 4-chloro-2'-methyl | 15 |
| 6 | methyl | H | H | TOPO | 15 | 160 | 4-methyl | 75 |
| 7 | methyl | H | 4-methyl | TOPO | 15 | 160 | 4,4'-dimethyl | 65 |
| 8 | phenoxy | H | 4-phenoxy | TOPO | 14 | 180 | 4,4'-diphenoxy | 50 |
| 9 | Br | | 4-methoxy | DsBF | 10 | 150 | 4-bromo-4'-methoxy | 20 |
| 10 | 1-Me | 4-Me | 4-Cl | DsBF | 15 | 145 | 2,5-dimethyl-4'-chloro | 85 |
| 11 | methoxy | H | 4-methyl | DsBF | 9 | 180 | 4-methoxy-4'-methyl | 88 |
| 12 | 1-methoxy | 3-methoxy | H | DsBF | 6 | 160 | 2,4-dimethoxy | 55 |
| 13 | 1-tert-amyl | 4-Me | H | DsBF | 6 | 160 | 5-tert-amyl-2-methyl | 55 |

Me = methyl
$^t$Bu = tert-butyl
DsBF = N,N-di-sec-butylformamide
TOPO = tri-n-octylphosphine oxide

We claim:

1. A process for preparing acylaromatic compounds from aromatic compounds and carboxylic acids, which comprises reacting the starting compounds with phosgene in the presence of an aliphatic phosphine oxide or of an N,N-dialkylformamide and of an Fe(II), Fe(III) or Zn(II) compound.

2. A process as claimed in claim 1, wherein the reaction is carried out in the presence of di-sec-butyl-formamide.

3. A process as claimed in claim 1, wherein the reaction is carried out in the presence of tri-n-butyl-, tri-n-hexyl- or tri-n-octylphosphine oxide.

4. A process as claimed in claim 1 wherein the reaction is carried out in the presence of $Fe_2O_3$.

* * * * *